(12) United States Patent
Krause-Heringer

(10) Patent No.: US 7,096,713 B2
(45) Date of Patent: Aug. 29, 2006

(54) TESTING ASSEMBLY AND CLAMPING FIXTURE FOR MEASURING FRICTION AND LOOSENING TORQUE AT DIFFERENT TEMPERATURES

(76) Inventor: Alexander Krause-Heringer, 2268 Catalpa Dr., Berkley, MI (US) 48072

( * ) Notice: Subject to any disclaimer, the term of this patent is extended or adjusted under 35 U.S.C. 154(b) by 85 days.

(21) Appl. No.: 10/825,927

(22) Filed: Apr. 14, 2004

(65) Prior Publication Data
US 2005/0229673 A1 Oct. 20, 2005

(51) Int. Cl.
*G01N 3/00* (2006.01)
(52) U.S. Cl. .............................................. 73/9
(58) Field of Classification Search ....... 73/9, 73/10, 826, 761, 828, 831; 33/787–790; 374/49–51
See application file for complete search history.

(56) References Cited

U.S. PATENT DOCUMENTS

| 4,393,716 | A | * | 7/1983 | Clark et al. .................... 73/818 |
| 4,603,588 | A | * | 8/1986 | Niermann et al. ............ 73/794 |
| 5,015,825 | A | * | 5/1991 | Brindley ..................... 219/390 |
| 5,345,826 | A | * | 9/1994 | Strong ......................... 73/826 |
| 5,388,464 | A | * | 2/1995 | Maddison .................... 73/856 |

* cited by examiner

*Primary Examiner*—Robert Raevis
(74) *Attorney, Agent, or Firm*—Clark Hill PLC

(57) ABSTRACT

A testing assembly measures the friction of a coating of a test piece having a defined length. The testing assembly comprises a base and a tower fixedly secured to the base. A receiving channel extends through the tower. The receiving channel has a predetermined diameter for receiving the test piece therein. The testing assembly also includes a port extending along a portion of the receiving channel. The port provides access to the test piece at various points along its defined length such that temperature readings of the test piece can be taken as torque and tension are measured.

19 Claims, 3 Drawing Sheets

TESTING ASSEMBLY AND CLAMPING FIXTURE FOR MEASURING FRICTION AND LOOSENING TORQUE AT DIFFERENT TEMPERATURES

BACKGROUND ART

1. Field of the Invention

The invention relates to a testing assembly for measuring frictional properties of a coating. More particularly, the invention relates to a testing assembly and a clamping fixture that can be used to accurately measure frictional properties of a coating at elevated temperatures.

2. Description of the Related Art

Many components that are manufactured require coatings to be applied to them after they have been manufactured. The primary purpose of a coating is to protect the manufactured piece from corrosion. Corrosion is the deterioration of a surface of an element over time. Corrosion occurs when the element interacts with environmental conditions. Such conditions may include oxidation, exposure to humidity and salt water. Corrosion may also occur when the thermal energy in the area surrounding the element is increased. And finally, mechanical damage to an element may cause the surface of that element to corrode.

Therefore, there is a need for a process for coating elements and components of manufacture such that their ability to interact with environmental conditions to further corrode the components is inhibited. Such coating may include paints, varnishes and other sealants. One problem that exists when coating a component is that the frictional properties of that component change. These properties are important to understand, especially if the component is going to be used in a hostile environment. This is typically the case when the component is designed to be incorporated into the manufacture of an automobile or aircraft. Components that are inside the engine compartment of a vehicle will experience severe changes in temperature. It would be detrimental to have a coating that would have a reduced coefficient of friction at elevated temperatures because components would become loose with ongoing operations of the vehicle.

Testing assemblies have been designed and manufactured to measure torque and tension, two measurements required to calculate the coefficient of friction. The torque measuring systems accurately determine the amount of torque required to loosen a nut from a bolt that are treated with a coating. These systems have limited usefulness when measuring components that are elevated in temperature. Should the components be heated, an accurate determination of the temperature cannot be made once the components are inserted into the torque testing systems. Therefore, there is a need in the art for a torque testing assembly that can more accurately test coatings for frictional properties through a myriad of temperatures.

SUMMARY OF THE INVENTION

A testing assembly measures the friction of a coating of a test piece having a defined length. The testing assembly includes a base and a tower fixedly secured to the base. A receiving channel extends through the tower. The receiving channel has a predetermined diameter for receiving the test piece therein. The testing assembly also includes a port extending along a portion of the receiving channel. The port provides access to the test piece at various points along its defined length such that temperature readings of the test piece can be taken as torque and tension are measured.

BRIEF DESCRIPTION OF THE DRAWINGS

Advantages of the invention will be readily appreciated as the same becomes better understood by reference to the following detailed description when considered in connection with the accompanying drawings, wherein.

DETAILED DESCRIPTION OF THE PREFERRED EMBODIMENT

Figure 1:
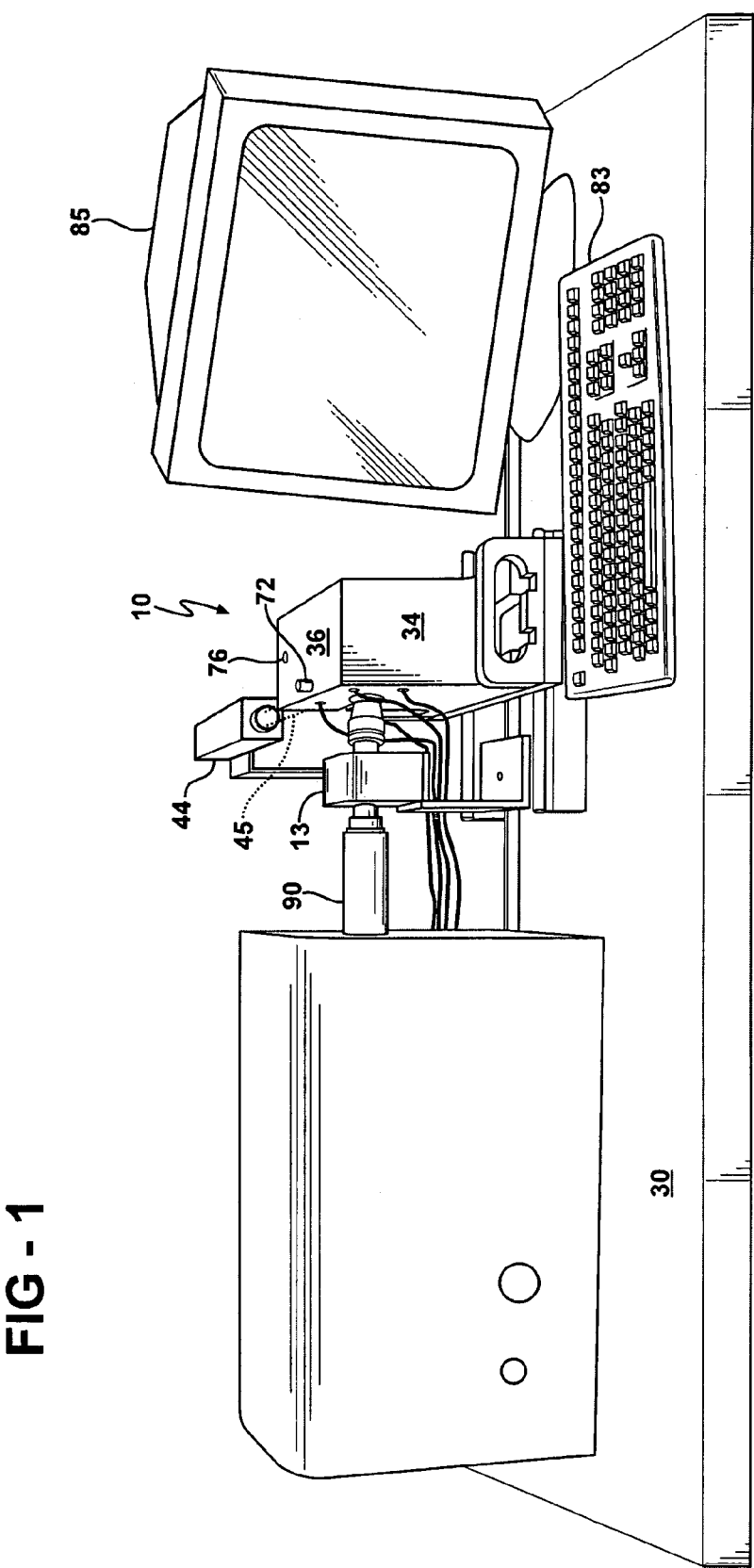
FIG. 1 is perspective view of one embodiment of the invention with a computer control and a mechanical drive torque wrench.
Figure 2:
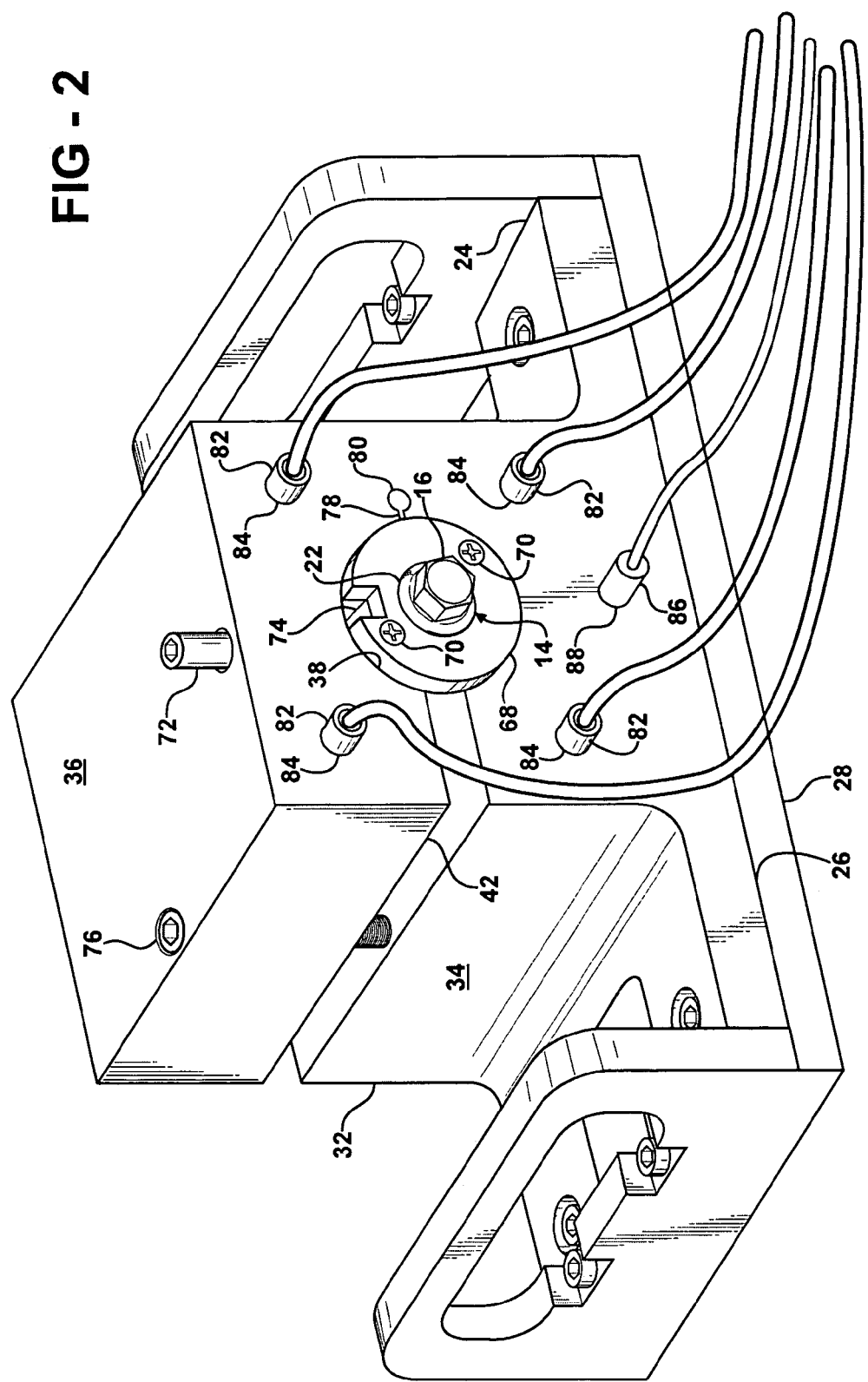
FIG. 2 is a side perspective view of the invention.
Figure 3:
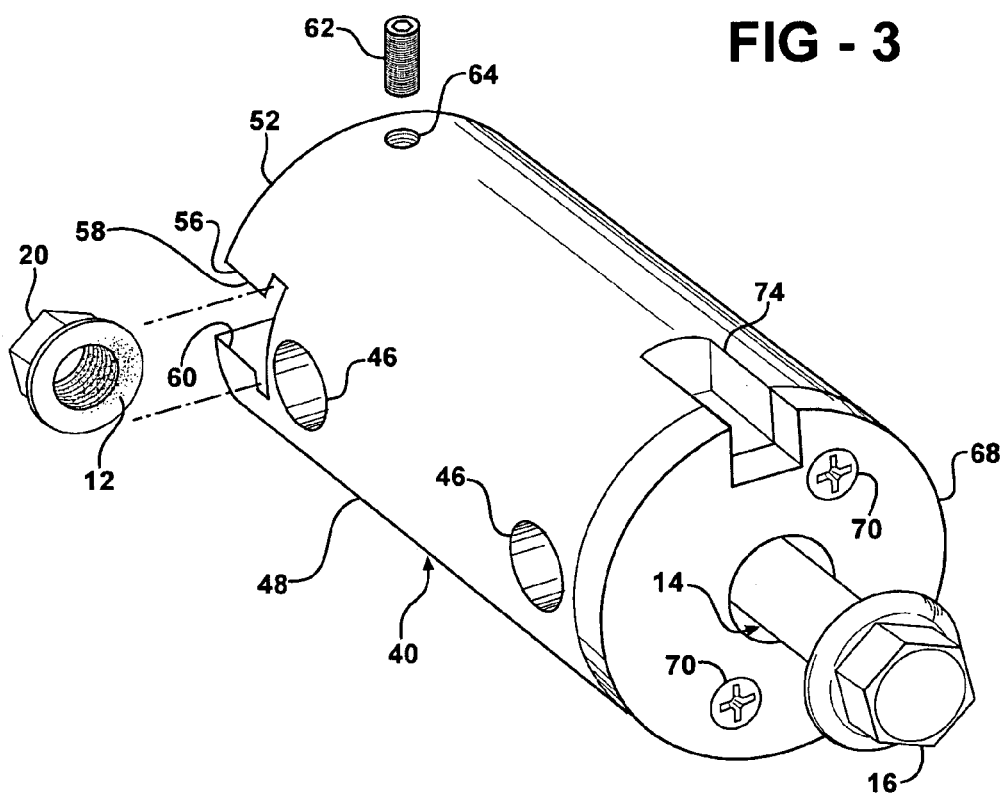
FIG. 3 is a partially exploded perspective view of a clamping fixture.

A testing assembly is generally indicated at 10 in the Figures. The testing assembly 10 measures friction of a coating 12 on a test piece, generally shown at 14. A torque measuring device 13 is used in conjunction with the testing assembly 10. The test piece 14 is shown to be a bolt in the Figures. It should be appreciated that the bolt 14 is shown by way of example and that other configurations of the test piece 14 may be used. For purposes of clarity, only a portion of the test piece 14 and nut 20 (discussed subsequently) are shown with the coating 12 applied thereto in stipple. The coating 12 may cover the entire test piece 14 and nut 20 or only a portion thereof.

The test piece 14 includes a head 16 and a fastener receiving end 18. In the embodiment shown, the test piece 14 shows the head 16 being a standard bolt head and the fastener receiving end 18 being a threaded end for receiving a nut 20 thereabout. The test piece 14 has a defined length from the head 16 to the fastener end 18. The test piece 14 may also include a washer 22 that is disposed adjacent the head 16. The test piece 14, nut 20 and washer 22 may be coated by the same coating 12 or different coatings, depending on the test being performed. The coating 12 is applied in a uniform manner so the test results can be as uniform as possible. In the embodiment shown in the Figures, the washer 22 is incorporated into the head 16.

The testing assembly 10 includes a base 24. The base 24 is rectangular in shape and defines a bottom surface 26. An insulator 28 is fixedly secured to the bottom surface 26 of the base 24. The insulator 28 prevents thermal energy received by the base 24 from passing through to a platform 30 to which the testing assembly 10 is secured.

The testing assembly 10 includes a tower 32 that extends upwardly from the base 24. The tower 32 defines four sides 34 and a tower top 36. The four sides 34 need to be treated specially so they will not interfere with infrared measurements, discussed subsequently. The tower 32 includes a receiving channel 38. The receiving channel 38 extends through the tower 32 and is accessible via two of the four sides 34. More specifically, the receiving channel 38 extends parallel to the base 24 along the entire width thereof. The receiving channel 38 has a predetermined diameter and receives the test piece 14 therein.

The testing assembly 10 also includes a clamping fixture 40. The clamping fixture 40 is removably insertable into the receiving channel 38 of the tower 32. The clamping fixture 40 secures the test piece 14 inside the clamping fixture 40 to accurately position the test piece 14 with respect to the testing assembly 10 within the receiving channel 38.

The testing assembly 10 also includes a port 42 that extends along a portion of the receiving channel 38. The port 42 provides access to the test piece 14 at various positions along the defined length of the test piece 14. The access allows temperature readings to be taken of the test piece 14 when torque and tension are being measured. An infrared sensing unit 44 receives infrared radiation 45 emanating from the test piece 14 through the port 42 to create measurements as to the temperature of the test piece 14. This allows the test piece 14 to be measured for its thermal energy along any point of its defined length in an accurate fashion.

The clamping fixture 40 includes an access opening 46. The access opening 46 allows the infrared radiation 45 from the test piece 14 to pass through the port 42 directly so that accurate measurements may be taken. In the preferred embodiment, there are two access openings 46, with one being disposed adjacent a portion of the clamping fixture 40 that is adjacent the head 16 and the other that is disposed at the other end of the clamping fixture 40 near the fastener receiving end 18 of the test piece 14. Alternatively, there may be a single access opening 46 that is oblong in shape extending along the length of the test piece 14. The dimensional relationship of the access opening 46 diameter with respect to the depth of thereof are calculated to create a constant infrared emissivity of the test piece 14 and coating 12 only.

The clamping fixture 40 defines a body 48 through which the access opening 46 extends. The body 48 has a predetermined length extending between the head receiving end 50 and a fastener receiving end 52. The body 48 defines a hollow core 54 that extends between the head receiving end 50 and the fastener receiving end 52. The hollow core 54 is designed to receive the test piece 14 therein.

The clamping fixture 40 also includes a fastener port 56 disposed at the fastener receiving end 52. The fastener port 56 receives the nut 20 therein. The fastener port includes interior walls 58, 60 that oppose each other on either side of the hollow core 54. The interior walls 58, 60 are designed to have two sides of a nut 20 abut thereagainst. A set screw 62 is inserted into a threaded hole 64 that extends between the body 48 through the interior wall 58. The set screw 62 is threaded through the threaded hole 64 to a position where it forces the nut 20 into an immoveable position with respect to the clamping fixture 40. This ensures the loosening procedure of the nut 20 does not spin before torque is applied. Thus, the frictional properties of the under head and thread friction are measured simultaneously. This allows an accurate measurement of the torque required to loosen the test piece 14 from the nut 20.

The head receiving end 50 of the clamping fixture 40 includes two screw holes 66. A plate 68 of known surface roughness is secured to the head receiving end 50 using screws 70 inserted into the screw holes 66. The plate 68 is used to remove one variable from the friction equation by setting a roughness of the clamping fixture 40 to a constant, thus enhancing the repeatability of the tests conducted using the testing assembly 10. The plate 68 may be replaced with other plates of identical roughness or varying roughness depending on the types of tests that are required. The screws 70 in the holes 66 with their head design ensures the plate 68 is centered on the head receiving end 50.

Returning attention to the tower 32, the receiving channel 38 has a predetermined diameter for receiving the test piece 14 and the clamping fixture 40 therein. The predetermined diameter of the receiving channel 38 is slightly larger than the outer diameter of the clamping fixture 40. The tower 32 also includes a locator pin 72. The locator pin 72 extends down from the tower top 36 into the receiving channel 38. The locator pin 72 is designed to properly orient the clamping fixture 40 within the receiving channel 38. The clamping fixture 40 includes an access orientation notch 74 that aligns the access opening 46 with the port 42 of the tower 32. This ensures that the access opening 46 aligns properly with the port 42 so the infrared beam of light 45 will directly impinge on a sensor within the infrared sensing unit 44.

The tower 32 includes a tower fastener 76 that secures the clamping fixture 40 within the receiving channel 38. The tower fastener 76 is a bolt that extends from the tower top 36 down through the port 42. Because the port 42 extends along an entire side 34, the tower 32 has the ability to clamp down on the clamping fixture 40. To facilitate the ability of the tower 32 to clamp the clamping fixture 40 thereto, the tower 32 includes a spring channel 78. The spring channel 78 extends through the entire tower 32 along a portion of the receiving channel 38. In one embodiment, the spring channel 78 is located along the receiving channel 38 directly opposite the port 42. The spring channel 78 is smaller in width than the port 42 as the tolerances between the receiving channel 38 and the clamping fixture 40 are minimal. The spring channel 78 includes a spring cylinder 80 disposed inwardly from the spring channel 78. The spring cylinder 80 cooperates with the spring channel 78 to facilitate the fastening of the clamping fixture 40 within the receiving channel 38 of the tower 32 and prevent stress cracks in the tower 32.

Thermal devices 82 are used to provide thermal energy to the tower 32 to maintain the test piece 14 at a desired temperature. The tower 32 includes thermal device receptacles 84 to receive the thermal devices 82 therein. In the embodiment shown, the thermal devices 82 are heat rods 82. The heat rod receptacles 84 extend into the tower 32 from one of its four sides 34. In the embodiment shown, the heat rod receptacles extend into the tower 32 at locations that are equidistant from and parallel to the receiving channel 38. A thermal couple 86 is inserted into a thermal couple receptacle 88 to provide feedback as to the amount of thermal energy received by the tower 32.

The heat rods 82, infrared gun 44 and a torque wrench 90 (discussed subsequently) are all electrically connected to control electronics (not shown) that may be housed under the platform 30. The control electronics may be operated using the keyboard 83 and monitor 85. It should be appreciated that other peripherals may be used in conjunction with the control electronics to facilitate the measuring and calculation of friction and temperature.

In operation, the test piece 14 is inserted into the hollow core 54 of the clamping fixture 40. A nut 20 is threaded onto the fastener receiving end 18 of the test piece 14. The test piece 14 is rotated to tighten the nut 20 thereon. The interior walls 58, 60 of the clamping fixture 40, in combination with the set screw 62, act as a wrench securing the nut 20 in a predetermined orientation such that rotation of the test piece 14 tightens the nut 20 thereon. Before tightening, the set screw 62 secures the nut 20 in position.

The clamping fixture 40 is then heated to a predetermined temperature, typically 150° C. The clamping fixture 40 may be heated by the heat rods 82 in the tower 32. Otherwise, the clamping fixture 40 and the test piece 14 are heated inside an oven independent of the testing assembly 10. Depending on where the clamping fixture 40 and test piece 14 are heated, the clamping fixture 40 is then inserted into the receiving channel 38 of the tower 32. The clamping fixture 40 is aligned such that the access orientation notch 74 receives the locator pin 72 therein assuring the access opening 46 is aligned with the port 42 of the tower 32.

The infrared sensing unit 44 then is aimed at the test piece 14 through the port 42 and access opening 46. Temperature readings are received by the measurements of the infrared beam 45 generated by the heated test piece 14 in the clamping fixture 40, which causes the emission of the infrared beam 45 proportional to the temperature of the test piece 14.

The torque measuring device 13 is used/driven by a drive 90 once the torque measuring device 13 is placed over the head 16 of the test piece 14. The torque measuring device 90 has measurement capabilities allowing it to measure the amount of torque generated at any given time. One torque wrench unit contemplated to be used in conjunction with the testing assembly 10 is one produced by TesT, of Erkrath, Germany. The amount of torque required to loosen the test piece 14 from the nut 20 is measured at a desired temperature: while 150° C. is a standard temperature at which these tests occur, it should be appreciated that these tests may occur at any temperature that measurement and calculations are desired. In addition, while the above disclosure discusses the thermal controlling devices as heat rods 82, it should be appreciated that these rods 82 may also be cooling devices should the desired test require temperatures less than ambient.

Figure 4:
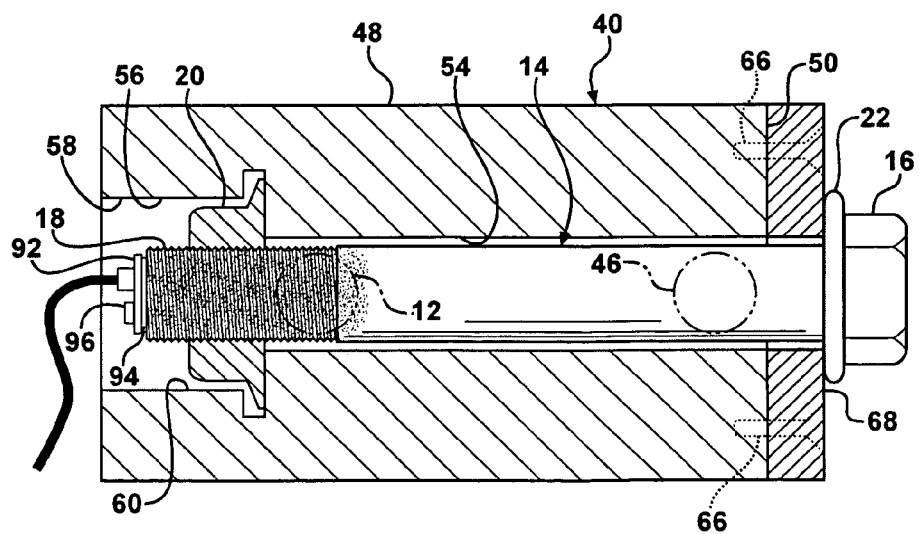
FIG. 4 is a cross-sectional side view of the clamping fixture.

Continuing with the operation, a tension sensor 92 (FIG. 4) is secured to one end of the test piece 14. The test tension sensor 92 may be secured to either the head 16 or the fastener receiving end 18 using an adhesive 94. In FIG. 4, the tension sensor is shown fixedly secured to the fastener receiving end 18. The tension sensor 92 measures the amount of tension on the test piece 14 as the torque wrench supplies its torque force to the head 16 of the test piece 14. The tension sensor 92 is a ultrasonic sensor that sends a sound wave through the test piece 14. A receiver 96 on the tension sensor 92 receives the ultrasonic signal generated thereby to determine how much tension the test piece 14 is under. One such tension sensor 92 is manufactured by Microcontrol, Inc. Using the formula for the coefficient of friction set forth below, the measurements of torque and tension are used:

$$\mu_{ges} = \frac{\frac{M_A}{F_V} - 0.159P}{(0.578 \cdot d_2) + \frac{D_{Km}}{2}},$$

wherein $\mu_{ges}$ is the coefficient of friction, $M_A$ is a tightening torque or loosing torque ($M_L$ would replace $M_A$ for loosening torque) for generating a load, $F_v$ is the proofing load, P is the pitch of the thread, $D_2$ is the bolt mean thread pitch diameter, and $D_{Km}$ is the mean diameter of the bearing face of the bolt head 16 or nut 20 relevant for frictional torque. The coefficient of friction $\mu_{ges}$ can be used for the assessment of the overall friction behavior of the test piece 14 and the nut 20. As such, the coefficient of friction for the coating 12 can be determined based on the result of the test piece 14. All of these data points also allow measuring a percentage torque retention at a given temperature by measuring the loosening torque at a given temperature.

The invention has been described in an illustrative manner. It is to be understood that the terminology, which has been used, is intended to be in the nature of words of description rather than of limitation.

Many modifications and variations of the invention are possible in light of the above teachings. Therefore, within the scope of the appended claims, the invention may be practiced other than as specifically described.

What is claimed is:

1. A testing assembly for measuring friction of a coating of a test piece having a defined length, said testing assembly comprising:
   a base;
   a tower fixedly secured to said base;
   a receiving channel extending through said tower, said receiving channel having a predetermined diameter for receiving the test piece therein; and
   a port extending along a portion of said receiving channel for accessing the test piece at various points along the defined length such that temperature readings of the test piece can be taken when torque and tension are measured.

2. A testing assembly as set forth in claim 1 including a clamping fixture that is received by said receiving channel, said clamping fixture securing the test piece therein to position the test piece with respect to said port.

3. A testing assembly as set forth in claim 2 wherein said clamping fixture includes an access opening providing access to the test piece secured therein.

4. A testing assembly as set forth in claim 3 wherein said clamping fixture includes an access orientation notch for aligning said access opening with said port of said tower.

5. A testing assembly as set forth in claim 4 including a locator pin extending through a portion of said tower and into said receiving channel to be received by said access orientation notch.

6. A testing assembly as set forth in claim 5 further including a tower fastener for securing said clamping fixture into said receiving channel.

7. A testing assembly as set forth in claim 6 further including a spring channel extending into said tower along said receiving channel for providing resiliency in said tower to clamp down on said receiving channel when said fastener secures said clamping fixture to said tower.

8. A testing assembly as set forth in claim 7 including thermal receptacles extending into said tower.

9. A testing assembly as set forth in claim 8 including thermal devices positionable inside said thermal receptacles to heat said tower when said test assembly is in operation.

10. A testing assembly as set forth in claim 9 wherein said thermal receptacles extend into said tower equidistantly about said receiving channel.

11. A testing assembly as set forth in claim 10 wherein said thermal receptacles extend into said tower parallel to said receiving channel.

12. A testing assembly as set forth in claim 11 including a thermocouple port for receiving a thermocouple sensor therein to measure thermal energy of said tower.

13. A testing assembly as set forth in claim 12 wherein said clamping fixture includes a set screw for securing a portion of the test piece to said clamping fixture.

14. A testing assembly as set forth in claim 13 including a thermal insulator fixedly secured to said base.

15. A testing assembly as set forth in claim 14 wherein said tower extends upwardly from said base.

16. A clamping fixture assembly, insertable into a tower having a port and a locator pin, to have a test piece and a fastener secured to said clamping fixture assembly, said clamping fixture assembly comprising:

a body having a predetermined length extending between a head receiving end and a fastener receiving end, said body defining a hollow core extending between said head receiving end and said fastener receiving end;

a fastener port disposed at said fastener receiving end for receiving a fastener therein;

an access opening in said body between said head receiving end and said fastener receiving end, said access opening providing access to said hollow core along said defined length allowing measurements of the test piece to be taken while the test piece is secured to said clamping fixture assembly;

a face plate securable to said head receiving end, said face plate having a defined roughness; and an access orientation notch for receiving the locator pin therein to orient said clamping fixture assembly with the tower to allow access via said access opening.

17. A clamping fixture assembly as set forth in claim 16 wherein said fastener port includes two parallel sides extending inwardly to prevent the fastener from substantial rotation about the test piece.

18. A clamping fixture assembly as set forth in claim 17 including a set screw channel extending through one of said two parallel sides, said set screw channel having a inner threaded surface.

19. A clamping fixture assembly as set forth in claim 18 including a set screw threadingly engaging said set screw channel to extend through said one of said two parallel sides to prevent the fastener from rotating with respect to said clamping fixture.

* * * * *